United States Patent [19]

Wirth

[11] Patent Number: 5,608,043

[45] Date of Patent: Mar. 4, 1997

[54] PROCESS FOR THE PREPARATION OF 2-DEOXY-2,2-DIFLUORO-β-D-RIBO-PENTOPYRANOSE COMPOUNDS

[75] Inventor: David D. Wirth, Lafayette, Ind.

[73] Assignee: Eli Lilly and Company, Indianapolis, Ind.

[21] Appl. No.: 649,934

[22] Filed: May 16, 1996

Related U.S. Application Data

[62] Division of Ser. No. 383,165, Feb. 3, 1995, Pat. No. 5,559,222.

[51] Int. Cl.$^6$ .............................. C07H 1/00; C07H 3/08
[52] U.S. Cl. .................... 536/4.1; 536/18.4; 536/18.5
[58] Field of Search ................... 536/4.1, 18.4, 536/18.5

[56] References Cited

U.S. PATENT DOCUMENTS

| | | | |
|---|---|---|---|
| 4,526,988 | 7/1985 | Hertel | 549/313 |
| 4,954,623 | 9/1990 | Nagarajan | 536/127 |
| 4,965,374 | 10/1990 | Chou et al. | 536/28.5 |
| 5,015,743 | 5/1991 | Hertel | 536/28.5 |
| 5,371,210 | 12/1994 | Chou | 536/27.11 |
| 5,401,838 | 3/1995 | Chou | 536/28.1 |
| 5,426,183 | 6/1995 | Kjell | 536/28.5 |
| 5,430,026 | 7/1995 | Hertel et al. | 536/28.5 |
| 5,434,254 | 7/1995 | Chou et al. | |

FOREIGN PATENT DOCUMENTS

| | | |
|---|---|---|
| 184365 | 6/1986 | European Pat. Off. . |
| 577303 | 1/1994 | European Pat. Off. . |

OTHER PUBLICATIONS

Helferich, B., "*Trityl Ethers of Carbohydrates*", in *Adv. Carb. Chem.*, 3, 79–III (1948).

Chou, T.S., et al., *Synthesis*, 6, 565–570 (1992).

Hertel, L.W., et al., *J. Org. Chem.*, 53, 2406–2409 (1988).

*Primary Examiner*—James O. Wilson
*Attorney, Agent, or Firm*—Margaret M. Brumm; David E. Boone

[57] ABSTRACT

A process for the preparation of 1-(2'-deoxy-2', 2'-difluoro-D-ribo-pentofuranosyl)-cytosine (VI) from 2-deoxy-2,2-difluoro-β-D-ribo-pentopyranose (I). The process uses a tritylation reaction (Step 3) for preparing 2-deoxy-2,2-difluoro-5-O-triphenylmethyl-ribo-pentofuranose (II) as a key intermediate. The 1-(2'-deoxy-2', 2'-difluoro-D-ribo-pentofuranosyl)-cytosine (VI) is an antiviral and anti-cancer agent.

8 Claims, No Drawings

PROCESS FOR THE PREPARATION OF 2-DEOXY-2,2-DIFLUORO-β-D-RIBO-PENTOPYRANOSE COMPOUNDS

This application is a division of application Ser. No. 08/383,165 filed Feb. 3, 1995, now U.S. Pat. No. 5,559,222.

BACKGROUND OF THE INVENTION

The present invention relates to the preparation of 1-(2'-deoxy-2', 2'-difluoro-D-ribo-pentofuranosyl)-cytosine (VI) from 2-deoxy-2,2-difluoro-β-D-ribo-pentopyranose (I) as a starting compound. In particular, the present invention relates to a process wherein 2-deoxy-2,2-difluoro-5-O-triphenylmethyl α- and β-D-ribo-pentofuranose (II) is prepared from the pentopyranose (I) by alkylation with triphenylmethyl chloride (tritylation). The 1-(2'-deoxy-2', 2'-difluoro-D-ribo-pentofuranosyl)-cytosine (VI) is an antiviral an anticancer agent.

Tritylation reactions are described by 3Helferich in *Adv. Carbohydrate Chemistry*, 3, 79–111 (1948). The reaction of a hydroxy group on an organic compound with triphenylmethyl chloride produces a triphenylmethyl ether. The reaction is commonly carried out in pyridine which acts as a solvent and an acid acceptor. The tritylation reactions are generally used with carbohydrates.

The preparation of 1-(2'-deoxy-2', 2'-difluoro-D-ribopentofuranosyl)-cytosine VI is described by Hertel et al, *J. Org. Chem.*, 53, 2406–2409 (1988) and Chou et al, *Synthesis*, 565–570 (June 1992). Different synthetic routes were used to prepare the compound (VI).

The preparation of 2-deoxy-2',2'-difluoro-β-D-ribo-pentopyranose (I) has been described in the literature. Thus, Hertel et al, *J. Org. Chem.*, 53, 2406–2409 (1988) and U.S. Pat. No. 4,954,623 to Nagarajan describe the preparation of pentopyranose (I).

It is therefore an object of the present invention to provide a process for the preparation of 1-(2'-deoxy-2',2'-difluoro-D-ribo-pentofuranosyl)-cytosine (VI) via an intermediate reaction using a tritylation reaction which produces a furanose (5-membered ring) product from a carbohydrate which otherwise exists mainly as a pyranose (6-membered ring). Further still, it is an object of the present invention to provide a process which produces 1-(2'-deoxy-2',2'-difluoro-D-ribo-pentofuranosyl)-cytosine (VI) in high yield. These and other objects will become increasingly apparent by reference to the following description.

SUMMARY OF THE INVENTION

The present invention relates to a process for the preparation of 2-deoxy-2,2-difluoro-5-O-triphenylmethyl-D-ribopentofuranose (II) which comprises: reacting in a reaction mixture 2-deoxy-2,2-difluoro-D-ribo pentopyranose (I) with triphenylmethyl chloride and with an amine base which can also be a solvent for the reaction mixture at a temperature between about 20° C. and 100° C. to produce (II); and separating (II) from the reaction mixture.

In particular the present invention relates to a process for producing 1-(2'-deoxy-2',2'-difluoro-D-ribo-pentofuranosyl)-cytosine (VI) and an alpha (β) isomer (VIA) from 2,2-difluoro-D-ribo-pentopyranose (II) which comprises reacting in a first reaction mixture 2-deoxy-2,2-difluoro-D-ribo-pentopyranose (I) with triphenylmethyl chloride and an amine base which is also a solvent for the reaction mixture at a temperature between about 20° C. and 100° C. to produce 2-deoxy-2,2-difluoro-5-O-triphenylmethyl-D-ribofuranose (II) and separating (II) from the first reaction mixture; reacting in a second reaction mixture (II) with methanesulfonyl chloride in the presence of an amine base in an organic solvent to form 2-deoxy-2,2-difluoro 3-O-methylsulfonyl-5-O-triphenyl methyl-D-ribo-pentofuranose-1-methanesulfonate (III) and separating (III) from the second reaction mixture; reacting in a third reaction mixture (III) with a protected cytosine in an inert solvent to form 1-(2'-deoxy-2',2'-difluoro-3'-O-methylsulfonyl-5-O-triphenyl methyl-D-ribo-furanosyl)-cytosine (IV) which is separated from the third reaction mixture; reacting (IV) in a fourth reaction mixture with an acid in the presence of an organic solvent to produce 1-(2'-deoxy-2',2'-difluoro-3'-O-methylsulfonyl-D-ribo-pentofuranosyl)-cytosine (V) and separating (V) from the fourth reaction mixture; and reacting (V) in a fifth reaction mixture with an alkali metal alkoxide in a solvent to form 1-(2'-deoxy-2',2'-difluoro-D-ribopentofuranosyl)-cytosine (VI and VIA) in the reaction mixture and separating (VI and VIA) from the fifth reaction mixture.

DETAILED DESCRIPTION PREFERRED EMBODIMENTS

The reaction(s) to produce intermediate (II) and 1-(2'-deoxy-2',2'-difluoro-D-ribo-pentofuranosyl)-cytosine (VI and VIA) are as follows:

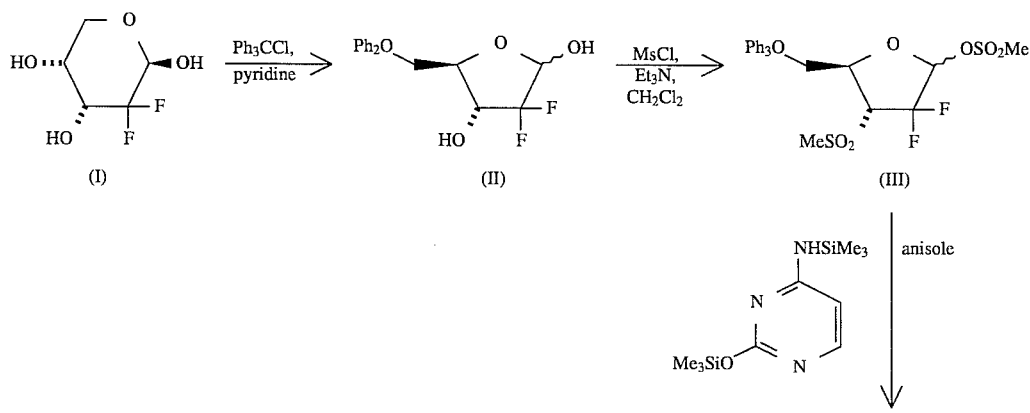

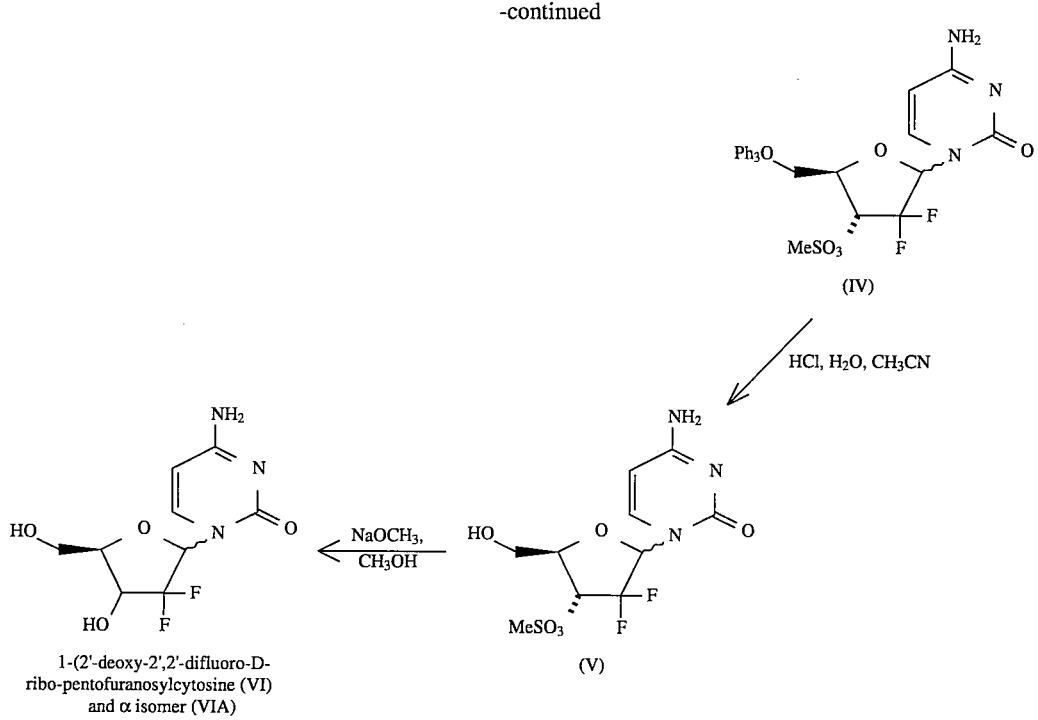

In preparing the 2-deoxy-2,2-difluoro-5-O-triphenylmethyl-D-ribo-pentofuranose (II) from 2,2-difluoro-D-ribo-pyranose (I), the reaction is conducted in the presence of an amine base which can act also as a solvent for the reaction at a temperature between 20° and 100° C. Such solvents are heterocyclic aromatic amines such as pyridine and 2-picoline. Additional solvents such as ethers (e.g. glyme), hydrocarbons (e.g. hexane), aromatic hydrocarbons (toluene, chlorobenzene) and esters (e.g. ethyl acetate) can be used to facilitate the mixing or workup of the reaction. Alkylamines such as triethylamine can also be used but are not preferred. In the reaction the base serves as an acid acceptor for hydrogen chloride generated in the reaction producing an amine hydrochloride salt. During the tritylation reaction, the six membered pyranose ring becomes a five membered furanose ring with a triphenylmethyl protecting group in the 5 position. It is believed that two key factors govern this transformation, namely the equilibration of the pyranose and furanose forms of the sugar (which greatly favor the undesired furanose form) and the fact that tritylation of primary alcohols is considerably faster than tritylation of secondary alcohols. Thus, since only the furanose form contains a primary alcohol group, it is preferentially tritylated and this reaction forces the equilibrium to an otherwise less stable position.

The α isomer (VIA) produced with the 1-(2'-deoxy-2',2'-difluoro-D-ribo-pentofuranosyl)-cytosine can be recycled. The process is described in Nagarjan U.S. Pat. No. 4,954,623. The intermediate product produced by the Nagarajan process is 2-deoxy-2,2-difluoro-ribo-pyranose (I).

General NMR spectra were recorded on a Bruker AC 300 spectrometer ($^1$H NMR at 300 MHz, $^{19}$F NMR at 282 MHz, $^{13}$C at 75 MHz). $^1$H NMR chemical shifts are reported in δ ppm relative to the solvent (acetone-$d_6$, 2.04 ppm; CDCl$_3$, 7.24 ppm; DMSO-$d_6$, 2.49 ppm). $^{19}$F NMR chemical shifts are reported in δ ppm relative to C$_6$F$_6$ (−162.9 ppm). $^{13}$C NMR chemical shifts are reported in δ ppm relative to the solvent (acetone-$d_6$, 29.8 ppm; CDCl$_3$, 77.0 ppm; DMSO-$d_6$, 39.5 ppm). Multiplicities are reported as s (singlet), brs (broad singlet), d (doublet), brd (broad doublet), t (triplet), dd (doublet of doublets), and dq (doublet of quartets). Flash chromatography was done on EM Science silica gel 60, 230–400 mesh, and TLC was performed on Merck glass-backed silica gel 60 plates, 0.25 mm thickness, with a 254 nm fluorescent indicator. Gas chromatography was performed on a HP5890 with a 30 m×0.1 mm ID DB1 capillary column with helium flow, a split injection, and flame ionization detection. The column temperature 50° C. for 3 minutes, 15° C./minute to 250° C., and held there for 5 minutes. HPLC was carried out using a Spectra-Physics SP8800 system with a Zorbax RX-C8 25 cm column and a 1.0 mL/minute flow rate. For intermediate compounds (II), (III) and (IV), the eluent was 60% buffer (50 mM NaH$_2$PO$_4$·H$_2$O, pH 5.0)/40% acetonitrile, and the detector was set to 254 nm. For compounds (V), (VI) and (VIA), the eluent was 90% buffer (50 mM NaH$_2$PO$_4$·H$_2$O, pH 5.0)/10% acetonitrile or 90% water/10% acetonitrile and the detector was set to 270 nm. Melting points were determined using a Meltemp device and are uncorrected.

Step 1

D-3,3-difluoro-4,5,6-trihydroxy-5,6-O-(1-ethylpropylidene)hexene

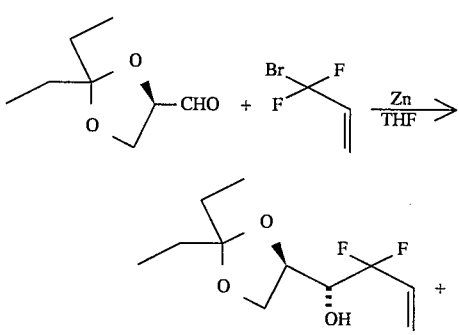

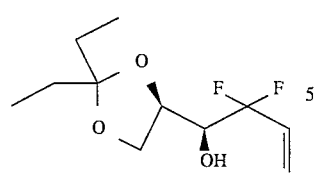
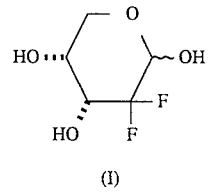

2-Deoxy-2,2-difluoro-β-D-ribo-pentopyranose (I).

A dry 250 mL round-bottomed flask fitted with a mechanical agitator, a reflux condenser, and a nitrogen purge was charged with 4.6 g zinc dust (70 mmol, 1.2 eq.), 9.3 g freshly distilled D-glyceraldehyde pentanide (59 mmol), and 100 mL anhydrous THF. 3-Bromo3,3-difluoropropene (6.6 mL, 65 mmol, 1.1 eq.) was added and the slurry stirred under nitrogen at ambient temperature for three days. To the flask was added 100 mL ether, 40 mL of a 5% aqueous solution of sodium bicarbonate, and about 2 g filter aid. The slurry was filtered, the cake washed with ether and water, and the layers separated. The aqueous layer was extracted with 10 mL ether and the combined ether layers were washed with 20 mL water. The solution was dried over anhydrous sodium sulfate and concentrated in vacuo to give 13.8 g yellow oil. The product was purified by taking a center cut from a vacuum distillation, bp 76°–81° C., 0.7 mm Hg. The yield of purified homoallylic alcohols was 5.7 g. The overall purity was 95% by GC and the erythro:threo ratio was 2.7:1 whereas it was 3.3:1 before distillation. The retention times on the GC were 12.96 minutes for threo and 13.16 minutes for erythro. Erythro: $^1$H NMR (CDCl$_3$) δ 6.15 (m, 1H), 5.85 (d, J=16 Hz, 1H), 5.62 (d, J=11 Hz, 1H), 4.4 (m, 1H), 4.2 (m, 1H), 4.1 (m, 1H), 1.75 (m, 4H), 1.05 (m, 6H). $^{19}$F NMR (DMSO-d$_6$) δ –108.6 (d,t J=250 Hz, J=15 Hz), –111.5 (t,d J=250 Hz, J=12 Hz). $^{13}$C NMR (CDCl$_3$) δ 130.2 (t, J=25 Hz), 129.9 (t, J=25 Hz), 121.0 (t, J=10 Hz), 120.7 (q, J=240 Hz), 112.7, 74.3, 73.1 (t, J=30 Hz), 65.4 29.4, 28.9, 8.1, 8.0. ms (EI) 207 (M-Et), 129, 57. Threo: $^1$H NMR (CDCl$_3$, δ 6.2 (m, 1H), 5.85 (d, J=16 Hz, 1H), 5.68 (d, J=12 Hz, 1H), 4.4 (m, 1H), 4.2 (m, 1H), 3.9 (m, 1H), 1.75 (m, 4H), 1.05 (m, 6H). $^{19}$F NMR (DMSO-d$_6$) δ –106.1 (d,t J=250 Hz, J=15 Hz), –111.3 (t,d J=250. Hz, J=12 Hz). $^{13}$C NMR (CDCl$_3$) δ 130.0 (t, J=25 Hz), 130.0 (t, J=25 Hz), 121.1 (t, J=10 Hz), 120.7 (q, J=240 Hz), 112.7, 74.2, 73.0 (t, J=30 Hz), 66.8, 29.5, 29.0, 8.1, 8.0. ms (EI) 207 (M-Et), 129, 57.

The 2.7:1 mixture of erythro and threo homoallylic alcohols (0.53 g, 2.2 mmol) of Step 1 was dissolved in about 50 mL methylene chloride and the solution placed in a 50 mL round-bottomed three-necked flask fitted with a sparge line and a magnetic stirrer. The solution was stirred in an ice bath and a stream of 2% ozone in air was sparged into the solution until a blue color persisted. After purging excess ozone, 7 mL of a 7% aqueous solution of sodium thiosulfate was added. After 5 minutes, the phases were separated, the lower layer washed with 10 mL water, and dried over anhydrous sodium sulfate. Removal of the solvent in vacuo at ambient temperature afforded 0.31 g of a colorless oil. The NMR spectra of this aldehyde (shown in brackets) in the reaction was complicated by hydrate formation but gc/ms analysis as above (in which hydrate would crack in the injection port) indicated the presence of the two diastereomeric aldehydes (ms, EI, 209, loss of Et). Acetonitrile (15 mL) and 1 mL water was added to the oil and the solution stirred at 53° C. overnight. The solution was evaporated under high vacuum to give 0.21 g of a colorless oil. Thin layer chromatography indicated two major pentopyranoses, R$_F$ 0.2 and 0.3 when the silica was eluted with toluene:isopropyl alcohol, 5:1. Authentic 2-deoxy-2,2-difluoro-β-D-ribopentopyranose (I) eluted with an R$_F$ of 0.2. The products were separated by flash chromatography on silica using the same solvent system to provide 40 mg of the sugar with R$_F$ 0.3 as a colorless oil and 100 mg of known sugar intermediate pentopyranose (I), R$_F$ 0.2 which was chromatographically and spectroscopically identical with authentic material.

2,2-difluoro deoxyxylose: R$_F$ 0.3; $^1$H NMR (acetone-d$_6$, D$_2$O) δ 5.05 (d, J=6.4 Hz), 3.9 (d,q J=22, 4.8 Hz, 1H), 3.85 (m, 2H), 3.72 (m, J=1.5 Hz, 1H). $^{13}$C NMR (acetone-d$_6$) 117.6 (q), 91.5 (q), 71.5 (t), 69.2 (t), 61.7 (s). $^{19}$F NMR (acetone-$_6$) δ–118.9 (d,d J=250, 4.9 Hz), –123.1 (d,d,d J=250, 22, 6.0 Hz).

(I) R$_F$ 0.2; mp 137–139° C.; $^1$H NMR (acetone-$_6$) δ 3.64 (1 H), 3.91 (1 H), 3.94 (1 H), 4.05 (1 H), 5.02 (1 H); $^{19}$F NMR (acetone-d$_6$) β –123.1 (brd, J$_{FF}$=253 Hz), –119.2 (dq, J$_{HF}$=3.7, 13.6 Hz, J$_{FF}$=250 Hz); $^{13}$C NMR (acetone-d$_6$) δ 63.56, 68.55, 68.55, 91.89, 117.30. Analysis for C5H8O4F2:

Calc.: C, 35.30; H, 4.74; F, 22.34;
Found: C, 35.59; H, 4.74; F, 22.52.

Step 2

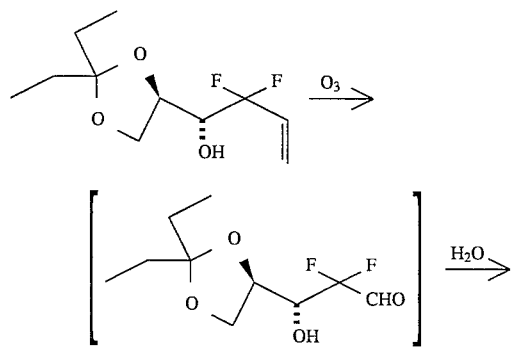

Step 3

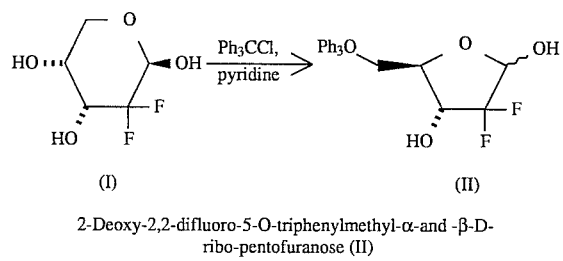

2-Deoxy-2,2-difluoro-5-O-triphenylmethyl-α-and -β-D-ribo-pentofuranose (II)

To a solution of 8.5 g of I (50 mmol) and 50 mL of pyridine which had stirred at 50° C for 2 hours was added of 15.3 g of triphenylmethyl chloride (55 mmol, 1.1 eq.). The reaction mixture was maintained at 50° C. under a nitrogen atmosphere for 20 hours. After the solution cooled to ambient temperature, it was poured into 50 mL of ice, and stirred until it reached ambient temperature. The aqueous layer was extracted with ether (3×50 mL). The combined organic layers were washed with phosphate buffer (2×100 mL 0.05 M $NaH_2PO_4$, pH 4), aqueous bicarbonate (4×100 mL $NaHCO_3$, saturated) and water (3×100 mL). It was dried with $MgSO_4$, and concentrated in vacuo to afford 23.1 g of II (47% yield) as an orange oil which formed a white solid upon standing at ambient temperature. The solid was shown by NMR to be mainly the α-anomer. Purification by flash chromatography (35% ethyl acetate/heptane) gave 3.9 g of pure II (83% yield) which had the following physical and spectral characteristics: $R_F$ 0.25 (35% ethyl acetate/heptane); mp 122–123° C.; $^1$H NMR (α-anomer, acetone-$d_6$) δ 3.24 (dd, 1 H, J=5.0, 5.3 Hz), 3.35 (dd, 1 H, J=3.0, 7.3 Hz), 4.18 (m, 1 H), 4.27 (m, 1 H), 5.02 (d, 1 H, J=6.2 Hz), 5.38 (t, 1 H, J=6.8 Hz), 6.12 (d, 1 H, J=6.4 Hz), 7.38 (m, 15 H); $^{19}$F NMR (α-anomer, acetone-$d_6$) δ–126.2 (dd, $J_{FF}$=240 Hz, $J_{HF}$=3.8 Hz), -110.5 (dq, $J_{FF}$=241 Hz, $J_{HF}$=5.8, 9.2 Hz); $^{13}$C NMR (α-anomer, acetone-$d_6$) δ 63.9, 72.5 (dd, J=20, 11 Hz), 82.0 (d, J=6.5 Hz), 87.2, 96.8 (q, J=21 Hz), 123.4 (t, J=248 Hz), 127.8, 128.6, 129.4, 144.8; $^1$H NMR (β-anomer, acetone-$d_6$) δ 3.3 (m, 2H), 3.98 (m, 1H), 4.4 (m, 1 H), 5.02 (d, 1 H), 5.21 (t, 1 H, J=7.1 Hz), 6.39 (d, 1 H, 6.3 Hz), 7.38 (m, 15 H); $^{19}$F NMR ( β-anomer, acetone-$d_6$) δ–127.4 (dq, $J_{FF}$=234 Hz, $J_{HF}$=5.7, 7.6 Hz), -125.7 (dd, $J_{FF}$=233 Hz, $J_{HF}$=3.4 Hz); MS m/z (α/βmixture, FD relative intensity) 412 (100), 243(15).

Analysis for $C_{24}H_{22}O_4F_2$:

Calc.: C, 69.89; H, 5.38; F, 9.21;

Found: C, 69.60; H, 5.48; F, 9.07.

Step 4

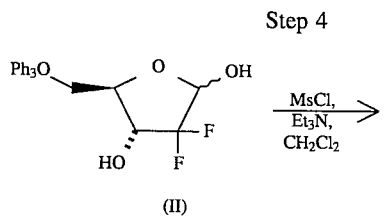

(II)

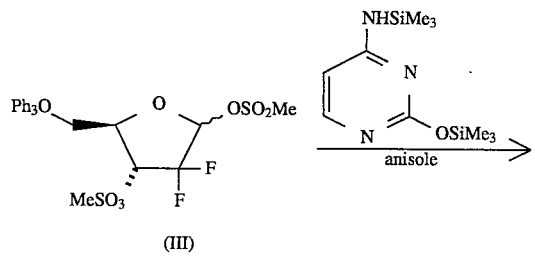

(III)

2-Deoxy-2,2-difluoro-3-O-methylsulfonyl-5-O-triphenylmethyl-α- and β-D-ribo-pentofuranose-1-methanesulfonate (III)

A 250 mL three-necked flask equipped with overhead stirrer, thermometer and addition funnel was charged with 3.0 g of pentofuranose (II) (7.3 mmol) and 120 mL of $CH_2Cl_2$. The mixture was stirred at room temperature until all solids had dissolved, and then was cooled to 0° C. To this solution was added dropwise 2.5 g of methanesulfonyl chloride (21.9 mmol, 3.0 eq. ) in 5 mL of $CH_2Cl_2$, while maintaining the temperature between 0° and 5° C. The addition funnel was rinsed with 5 mL of $CH_2Cl_2$, and 2.2 g of triethylamine (21.9 mmol, 3.0 eq. ) was added dropwise, maintaining the temperature below 5° C., followed by an additional 5 mL $CH_2Cl_2$ rinse. The mixture was warmed to ambient temperature and stirred for 1.5 hours. The solution was washed (5×150 mL $NaHCO_3$, saturated), dried with $MgSO_4$ and concentrated in vacuo, yielding 4.0 g pentofuranose-1-methanesulfonate, (III) (88% yield) as a white solid. Purification by flash chromatography (5% ether/toluene) afforded 0.3 g β-anomer of pentofuranose-1-methanesulfonate (III), which decomposed upon standing, and 1.0 g α-anomer of pentofuranose-1-methanesulfonate (III) (50% yield), which had the following spectral characteristics: $R_F$0.3 (5% ether/toluene); $^1$H NMR (CDCl$_3$), δ 3.02 (s, 1 H), 3.07 (s, 1 H), 3.44 (dd, 2 H, J=3.9, 7.1 Hz), 4.48 (q, 1 H, J=4.1 Hz), 5.20 (dd, 1 H, J=4.5, 11.2 Hz), 6.09 (d, 1 H, J=6.0 Hz), 7.38 (m, 15 H) ; $^{19}$F NMR (CDCl$_3$) δ–121.5 (d, $J_{FF}$=255 Hz), –108.7 ($J_{FF}$=256 Hz, $J_{HF}$=5.8, 9.9 Hz); $^{13}$C NMR (CDCl$_3$) δ 38.7, 40.2, 60.8, 74.6 (q, J=19 Hz ), 83.2, 87.3, 99.0 (q, J=23 Hz ), 143.0; FAB MS m/z (relative intensity) 568 (1.2), 491 (2.6), 395 (0.6), 243 (100), 155 (19), 119 (34).

Analysis for $C_{26}H_{26}O_8S_2F_2$:

Calc.: C, 54.92; H, 4.61; S, 11.28; F, 6.68;

Found C, 55.17; H, 4.86; S, 10.98: F, 6.64.

Step 5

1-[2'-deoxy-2',2'-difluoro-3'-O-methylsulfonyl-5'-O-triphenylmethyl-α- and β-D-ribopentofuranosyl]-cytosine (IV)

A 50 mL four-necked flask equipped with thermometer, heating mantle, condenser, and overhead stirrer was charged with 2.6 g of cytosine (23.2 mmol, 22 eq.), 15.2 mL of hexamethyldisilazane (72 mmol, 68.2 eq.) and 2.6 mg of $(NH_4)_2SO_4$ (0.02 mmol, 0.015 eq.). The mixture was heated to 120° C. and stirred until the solution was clear (1.5 hours). The solution was then heated to 145° C. and excess HMDS was removed by distillation. When atmospheric distillation ceased, the temperature was reduced to 120° C., and HMDS was distilled in vacuo until no visible liquid remained in the reaction vessel. To the solid silylated cytosine was added 2.1 mL of anisole and the slurry was stirred at 110° C. until all solids had dissolved. A solution of 0.6 g of pentofuranose-1-methanesulfonate intermediate (III) (1.06 mmol) in 0.8 mL of anisole was added and the mixture was stirred at 110° C. for 4.5 hour. The reaction mixture was diluted with 8 mL of anisole; the solution was reheated to 110° C. and poured slowly into 30 mL water at 0° C. An additional 35 mL of water was added, and the mixture was stirred at 90° C. until all solids dissolved. The hot layers were separated and the organic solution was concentrated in vacuo, providing 0.43 g of crude cytosine intermediate (IV) (40% yield) as an orange-yellow oil. Flash chromatography (20% 2-propanol/chloroform) provided 100 mg of the β-anomer, 40 mg of the α-anomer, and 240 mg of a pure α/β mixture of cytosine (IV).

The following physical and spectral characteristics were observed for the α-anomer: $R_f$ 0.32 (20% 2-propanol/chloroform); $^1$H NMR (DMSO-$d_6$) δ 3.25 (s, 1 H), 3.4 (m, 2 H), 4.76 (m, 1 H), 5.55 (q, 1 H, J=7.5 Hz), 5.83 (d, 1 H, J=7.5 Hz), 6.50 (dd, 1 H, J=7.2, 2.4 Hz), 7.4 (m, 15 H), 7.5 (s, 2 H), 7.6 (d, 1 H); $^{19}$F NMR (DMSO-$d_6$) δ –121.4 (brd, $J_{FF}$=235 Hz), –112.8 (brd, $J_{FF}$=198 Hz); $^{13}$C NMR (DMSO-$d_6$,) δ 37.9, 62.2, 75.4 (q, J=15 Hz), 79.6, 83.5 (q, J=19 Hz), 86.6, 94.9, 121.1 (t, J=261 Hz), 127.2, 128.0, 128.2, 140.9, 143.9, 154.6, 165.8.

The following physical and spectral characteristics were observed for the β-anomer: $R_f$ 0.41 (20% 2-propanol/chloroform); $^1$H NMR (DMSO-$_6$) δ 3.21 (s, 1 H), 3.43 (m, 2 H), 4.32 (m, 1 H), 5.46 (q, 1H, J=9.0 Hz), 5.75 (d, 1 H, J=7.5), 6.26 (t, 1 H, J=8.5), 7.3 (m, 15 H), 7.50 (s, 2 H), 7.59 (d, 1 H, J=7.5); $^{19}$F NMR (DMSO-$d_6$) δ –114.2 (brs, 2 F); $^{13}$C NMR (DMSO-$d_6$) δ 38.0, 61.6, 74.5 (t, J=24 Hz), 76.3 86.7, 95.0, 121.0 (t, J=261 Hz), 127.2, 128.0, 128.2, 143.1, 154.3, 165.8; FAB MS m/z (relative intensity) 584 (17), 342 (5), 243 (100), 155 (12), 133 (46). HRMS Calcd for $C_{29}H_{28}N_3O_6SF_2$: 584.1667. Found: 584.1692.

Step 6

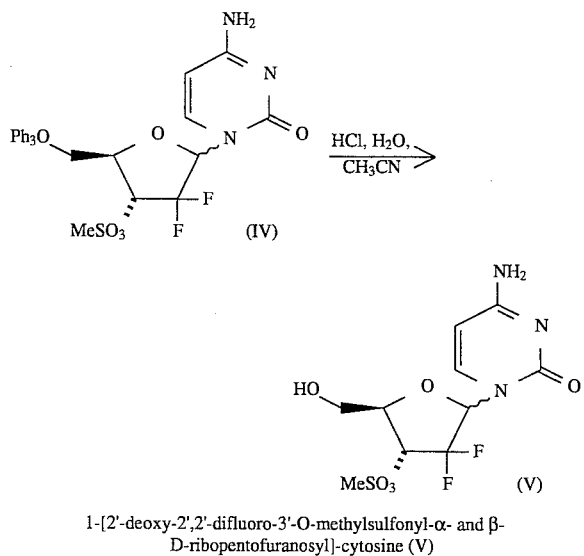

1-[2'-deoxy-2',2'-difluoro-3'-O-methylsulfonyl-α- and β-D-ribopentofuranosyl]-cytosine (V)

A 10 mL single-necked flask equipped with condenser, magnetic stirrer, temperature probe, and nitrogen inlet was charged with 0.33 g of cytosine intermediate (IV) (0.6 mmol) and 2 mL acetonitrile. The pH was adjusted to 1.0 with HCl (5% aq). The solution was heated to reflux and stirred for 3 hours. The solution cooled to ambient temperature and 4 mL water was added to precipitate triphenylmethanol. The solution was filtered after stirring at ambient temperature for 15 minutes. The precipitate was washed with water (2×2 mL), and the combined filtrates were concentrated in vacuo, providing 150 mg of cytosine intermediate (V) (45% yield).

Physical and spectral characteristics (α-anomer): $^1$H NMR (DMSO-$d_6$), δ 3.4 (s, 1 H), 3.72 (m, 2H), 4.64 (m, 1 H), 5.49 (q, 1 H, J=8.0 Hz), 6.24 (d, 1H), 6.36 (t, 1H, J=6.7 Hz), 7.99 (d, 1 H, J=7.8 Hz), 8.86 (s, 1H), 9.97 (s, 1H); $^{19}$F NMR (DMSO-$d_6$) δ–120.4 (d, $J_{FF}$=240 Hz), –113.5 (d, $J_{FF}$=241 Hz);

Physical and spectral characteristics (α-anomer): $^1$H NMR (DMSO-$d_6$), δ 3.4 (s, 1H), 3.72–3.82 (m, 2H), 4.28 (m, 1H), 5.30 (q, 1 H, J=9.1 Hz), 6.24 (d, t, 2H), 8.06 (d, 1 H, J=7.8 Hz), 8.86 (s, 1 H), 9.94 (s, 1 H); $^{19}$F NMR (DMSO-$d_6$) δ —114.1 (brs, 2 F); $^{13}$C NMR (DMSO-$d_6$) δ 38.2, 59.8, 74.1 (t, J=24 Hz), 79.4, 84.1 (t, J=31 Hz), 95.4, 121.0 (t, 262 Hz), 144.2, 147.0, 160.0.

Step 7

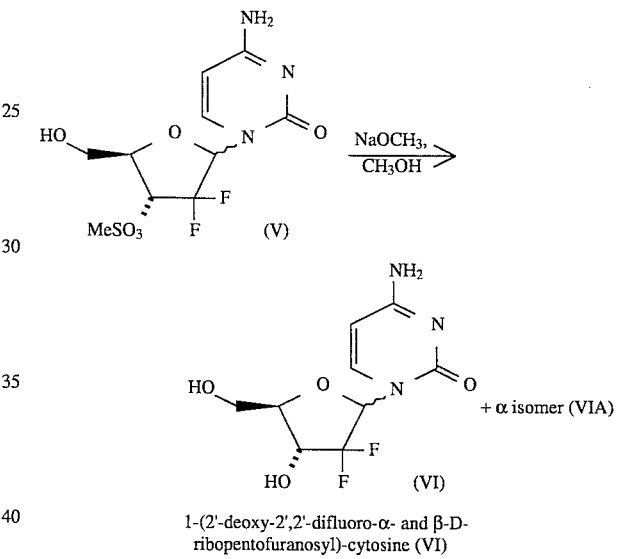

1-(2'-deoxy-2',2'-difluoro-α- and β-D-ribopentofuranosyl)-cytosine (VI)

A 10 mL single-necked flask equipped with condenser, and nitrogen inlet was charged with 0.28 g of intermediate V and 4.2 mL of CH$_3$OH. The pH was adjusted to 11 with NaOCH$_3$ (saturated CH3OH solution), and the solution was heated to reflux and stirred for 24 hours. After cooling to ambient temperature, 4 mL of 2-propanol was added, and the cloudy solution was stirred at 0° C. for 45 minutes. The slurry was filtered through filter aid. To the filtrate was added concentrated HCl to give a pH of 1. After stirring the resultant slurry at 0° C. for 2 hours, the solid product was filtered and washed with 0.4 mL of 2-propanol. The yield was 33 mg of cytosine product (VI) (10% yield), containing 98% β-anomer and ~2% α-anomer, and having the following spectral characteristics: $^1$H NMR (DMSO-$d_6$) δ 3.63 (dd, 1 H, J=3.2, 9.5 Hz), 3.77 (d, 1 H, J=12.3 Hz), 3.89 (d, 1 H, 8.2 Hz), 4.19 (m, 1 H), 6.05 (t, 1 H, J=7.1 Hz), 6.31 (d, 1 H, J=7.9 Hz), 8.18 (d, 1 H, J=7.9 Hz), 9.06 (s, 1 H), 10.28 (s, 1 H). Its retention time on HPLC was identical to an authentic sample of cytosine product (VI).

The foregoing description is only illustrative of the present invention and the present invention is limited only by the hereinafter appended claims.

I claim:

1. A process for the preparation of 2-deoxy-2,2-difluoro-5-O-triphenylmethyl-D-ribo-pentofuranose (II) which comprises:

(a) reacting in a reaction mixture 2-deoxy-2,2-difluoro-D-ribopentopyranose (I) with triphenylmethyl chloride and an amine base at a temperature between about 20° C. and 100° C. to produce (II); and (b) separating (II) from the reaction mixture.

2. The process of claim 1 wherein the base is pyridine.

3. The process of claim 1 wherein in step (b) the reaction mixture from step (a) is poured over ice and the (II) is extracted from the reaction mixture using an organic solvent.

4. The process of claim 3 wherein the solvent is diethyl ether.

5. The process of claim 1 wherein in step (b) the (II) is a mixture of α- and β-anomers which are separated from each other chromatographically.

6. The process of claim 1 wherein in step (a) the base is pyridine and wherein the reaction mixture from step (a) is poured over ice and (II) is extracted from the reaction mixture using diethyl ether.

7. 2-Deoxy-2,2-difluoro-5-O-triphenyl methyl-D-ribo-pentofuranose.

8. 2-deoxy-2,2-difluoro-3-O-methylsulfonyl-5-O-triphenyl methyl-D-ribopentofuranose-1-methanesulfonate.

* * * * *